(12) United States Patent
Tiwari et al.

(10) Patent No.: US 11,534,404 B2
(45) Date of Patent: Dec. 27, 2022

(54) MULTILAYER BEADS FOR PHARMACEUTICAL USE

(71) Applicant: Sucampo AG, Zug (CH)

(72) Inventors: Deepak Tiwari, Rockville, MD (US); Yasuhiro Harada, Chiyada-ku (JP); Ryu Hirata, Hyogo (JP)

(73) Assignee: Sucampo AG, Zug (CH)

( * ) Notice: Subject to any disclaimer, the term of this patent is extended or adjusted under 35 U.S.C. 154(b) by 0 days.

(21) Appl. No.: 16/338,948

(22) PCT Filed: Oct. 5, 2017

(86) PCT No.: PCT/IB2017/001383
§ 371 (c)(1),
(2) Date: Apr. 2, 2019

(87) PCT Pub. No.: WO2018/065826
PCT Pub. Date: Apr. 12, 2018

(65) Prior Publication Data
US 2020/0390708 A1 Dec. 17, 2020

Related U.S. Application Data

(60) Provisional application No. 62/405,131, filed on Oct. 6, 2016.

(51) Int. Cl.
A61K 9/16 (2006.01)
A61K 9/50 (2006.01)
A61K 31/558 (2006.01)
A61K 9/00 (2006.01)

(52) U.S. Cl.
CPC .......... *A61K 9/1676* (2013.01); *A61K 9/1611* (2013.01); *A61K 9/1635* (2013.01); *A61K 9/1652* (2013.01); *A61K 9/5026* (2013.01); *A61K 31/558* (2013.01); *A61K 9/0053* (2013.01)

(58) Field of Classification Search
CPC .................................................. A61K 9/1676
See application file for complete search history.

(56) References Cited

U.S. PATENT DOCUMENTS

| 5,252,605 | A | 10/1993 | Ueno |
| 5,317,032 | A | 5/1994 | Ueno et al. |
| 6,414,016 | B1 | 7/2002 | Ueno |
| 6,583,174 | B1 | 6/2003 | Ueno et al. |
| 6,596,056 | B2 | 7/2003 | Domesle et al. |
| 7,064,148 | B2 | 6/2006 | Ueno et al. |
| 8,026,393 | B2 | 9/2011 | Hashitera et al. |
| 2012/0208773 | A1* | 8/2012 | Duffield ............. A61K 21/4745 514/21.2 |
| 2016/0310559 | A1* | 10/2016 | Fretzen .................. A61K 38/10 |
| 2017/0348263 | A1* | 12/2017 | Ohlstein .............. A61K 31/196 |

FOREIGN PATENT DOCUMENTS

| EP | 2275419 A2 | 1/2011 |
| WO | 2001/076593 A2 | 10/2001 |
| WO | 2002/089812 A1 | 11/2002 |
| WO | 2007/086536 A2 | 8/2007 |
| WO | 2016/067620 A1 | 5/2016 |
| WO | 2018/065826 A1 | 4/2018 |

OTHER PUBLICATIONS

Anastasia Rivkin, Lubiprostone: Chloride Channel Activator for Chronic Constipation, Clinical Therapeutics/vol. 28, No. 12, 2006 (Year: 2006).*
John Cuppoletti, Contrasting effects of linaclotide and lubiprostone on restitution of epithelial cell barrier properties and cellular homeostasis after exposure to cell stressors, BMC Pharmacology 2012, 12:3 (Year: 2012).*
USFDA Guidance for Industry, "Size of Beads in Drug Products Labeled for Sprinkle", May 2012, 7 pages.
Rivkin A et al: "Lubiprostone: Chloride channel activator for chronic constipation", Clinical Therapeutics, 2006, vol. 28, No. 12, pp. 2008-2021.
International Search Report and Written Opinion dated Jul. 2, 2018 for related International Application WO 2018/065826 11 pages.

* cited by examiner

*Primary Examiner* — Mark V Stevens
*Assistant Examiner* — Alparslan Asan

(57) ABSTRACT

Multilayer beads for pharmaceutical use having a drug-in-polymer layer are disclosed. The disclosed multilayer beads for pharmaceutical use have (a) a core particle; (b) an optional barrier layer coated on the surface of the core particle; (c) a drug-in-polymer layer coated on the surface of the core or the barrier layer, (d) an optional sealant layer coated on the surface of the drug-in-polymer layer; and (e) optionally one or more outer layers external to the drug-in-polymer layer or the sealant layer. The drug-in-polymer layer consists essentially of (i) a drug selected from the group consisting of a 15-keto prostaglandin drug, a 13,14-dihydro prostaglandin drug, and a 13,14-dihydro-15-keto prostaglandin drug; and (ii) a polymer selected from the group consisting of polyvinylpyrrolidone, vinylpyrrolidone-vinylacetate copolymer or a mixture thereof. The drug-in-polymer layer may be solid dispersion of the drug in the polymer. Pharmaceutical compositions comprising a plurality of multilayer beads and a pharmaceutically acceptable excipient and methods of treating a gastrointestinal disorder are also disclosed.

27 Claims, 2 Drawing Sheets

MULTILAYER BEADS FOR PHARMACEUTICAL USE

CROSS-REFERENCE TO RELATED APPLICATIONS

This application is a U.S. National Stage Application of International Application No. PCT/IB2017/001383, filed Oct. 5, 2017, which claims the priority of U.S. Provisional Patent Application Ser. No. 62/405,131, filed Oct. 6, 2016, the disclosure of each is hereby incorporated by reference in its entirety.

FIELD OF THE INVENTION

The invention relates to multilayer beads, and processes for their preparation, and pharmaceutical uses thereof. More particularly, the invention relates to multilayer beads having a drug-in-polymer layer where the drug is a 15-keto prostaglandin drug, a 13,14-dihydro prostaglandin drug, or a 13,14-dihydro-15-keto prostaglandin drug and the polymer is polyvinylpyrrolidone, vinylpyrrolidone-vinylacetate copolymer or a mixture thereof and used to treat gastrointestinal disorders.

BACKGROUND

Fatty acid derivatives are found in tissues or organs of humans and other mammals, and exhibit a wide range of physiological activities. Prostaglandins are a type of fatty acid derivative, having a prostanoic acid skeleton as shown in the formula (A):

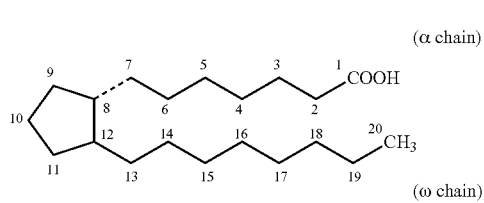

Some synthetic prostaglandin (PG) analogues have modified prostanoic acid skeletons and various chemical modifications. The primary structures of such analogues are classified as PGAs, PGBs, PGCs, PGDs, PGEs, PGFs, PGGs, PGHs, PGIs and PGJs according to the five-membered ring moiety, and they can be further classified into subtypes by the number and position of an unsaturated bond on the omega chain.

Derivatives of $PGE_1$ are used to treat gastrointestinal disorders. For example, 15-keto-16-halogen prostaglandin compounds are useful as cathartics (U.S. Pat. No. 5,317,032). Lubiprostone, also known as 13,14-dihydro-15-keto-16,16-difluoro-$PGE_1$, is the active pharmaceutical ingredient ("API" or "drug substance") in the Amitiza® drug product used for the treatment of conditions such as chronic idiopathic constipation, opioid-induced constipation and irritable bowel syndrome in adults. Lubiprostone activates the Type 2 Chloride Channel (ClC-2) and increases chloride-rich fluid secretion from the serosal to the mucosal side of the gastrointestinal tract.

In general, prostaglandins are insoluble in water and become significantly unstable in the presence of water. Moreover, prostaglandins are unstable themselves or in the presence of most solids or solvents. To address such challenges, an encapsulated formulation comprising a 15-keto-16-difluoro prostaglandin compound and a solvent such as glyceride, which can maintain the stability of the compound, was described (U.S. Pat. No. 6,583,174). Amitiza is formulated with medium chain fatty acid triglycerides (MCTs) in a soft-gelatin capsule with a high shelf stability as described in U.S. Pat. No. 8,026,393.

Some patient populations, for example, pediatric or geriatric, have an inability to swallow capsules or tablets. This can complicate, reduce or even eliminate the possibility of treatment. There is a need to develop new formulations which allow prostaglandins to be easily administered and to serve such patient populations. This invention addresses that need.

SUMMARY OF THE INVENTION

The invention relates to multilayer beads for pharmaceutical use having a drug-in-polymer layer where the drug is a 15-keto prostaglandin drug, a 13,14-dihydro prostaglandin drug, or a 13,14-dihydro-15-keto prostaglandin drug and the polymer is polyvinylpyrrolidone, vinylpyrrolidone-vinylacetate copolymer or a mixture thereof. More broadly, the invention is applicable to fatty acid derivatives used as drugs and described in Formula I of U.S. Pat. No. 8,026,393, the contents of which are expressly incorporated by reference. The invention also relates to pharmaceutical compositions containing a plurality of the multilayer beads and are used to treat gastrointestinal disorders, especially gastrointestinal disorders in children, the elderly and individuals with dysphagia.

The invention provides multilayer beads for pharmaceutical use comprising:
(a) a core particle;
(b) an optional barrier layer coated on the surface of the core particle;
(c) a drug-in-polymer layer coated on the surface of the core particle or, when present, the barrier layer, wherein the drug-in-polymer layer consists essentially of:
  (i) a drug selected from the group consisting of a 15-keto prostaglandin drug, a 13,14-dihydro prostaglandin drug, and a 13,14-dihydro-15-keto prostaglandin drug; and
  (ii) a polymer selected from the group consisting of polyvinylpyrrolidone, vinylpyrrolidone-vinylacetate copolymer or a mixture thereof;
(d) an optional sealant layer coated on the surface of the drug-in-polymer layer; and
(e) optionally, one or more outer layers external to the drug-in-polymer layer or, when present, the sealant layer.

The invention provides pharmaceutical compositions comprising a plurality of multilayer beads and a pharmaceutically acceptable excipient. The plurality of multilayer beads in combination represent a therapeutically effective amount of the drug and may be a unit dose of the drug. Such a pharmaceutical composition is usually presented in the form of a solid oral dosage form.

The invention also relates to methods of treating a gastrointestinal disorder comprising the step of orally administering to a patient in need thereof a therapeutically effective amount of the multilayer beads in a pharmaceutical composition of according to the invention.

Another embodiment of the invention relates to a solid formulation or a solid dispersion of a drug in a polymer consisting essentially of (a) a drug selected from the group consisting of a 15-keto prostaglandin drug, a 13,14-dihydro prostaglandin drug, and a 13,14-dihydro-15-keto prostaglandin drug; and (b) a polymer selected from the group consisting of polyvinylpyrrolidone, vinylpyrrolidone-vinylacetate copolymer or a mixture thereof.

DESCRIPTION OF THE INVENTION

The invention relates to multilayer beads for pharmaceutical use having a drug-in-polymer layer where the drug is a 15-keto prostaglandin drug, a 13,14-dihydro prostaglandin drug, or a 13,14-dihydro-15-keto prostaglandin drug and the polymer is polyvinylpyrrolidone, vinylpyrrolidone-vinylacetate copolymer or a mixture thereof. More broadly, the invention is applicable to fatty acid derivatives used as drugs and described in Formula I of U.S. Pat. No. 8,026,393, the contents of which are expressly incorporated by reference. The invention is based on a finding that such beads and drug formulations are surprisingly effective to stabilize the drug and to prevent it from migrating outside of the drug-in-polymer layer. The invention also relates to pharmaceutical compositions containing a plurality of the multilayer beads and are used to treat gastrointestinal disorders, especially gastrointestinal disorders in children and the elderly.

15-keto prostaglandin drugs, 13,14-dihydro prostaglandin drugs and 13,14-dihydro-15-keto prostaglandin drugs are known in the art and are known to be effective in treating gastrointestinal disorders. These drugs, which are derivatives of fatty acids, are described in published PCT application WO 2016/067620 and U.S. Pat. No. 6,414,016; the disclosures of which are incorporated herein by reference. Representative examples of these drugs include but are not limited to:

(−)-7-[(2R,4aR,5R,7aR)-2-(1,1-difluoropentyl)-2-hydroxy-6-oxooctahydrocyclopenta[b]pyran-5-yl]heptanoic acid, (lubiprostone);

(−)-7-{(2R,4aR,5R,7aR)-2-[(3S)-1,1-difluoro-3-methylpentyl]-2-hydroxy-6-oxooctahydrocyclopenta[b]pyran-5-yl}heptanoic acid, (cobiprostone);

(+)-isopropyl (Z)-7-[(IR,2R,3R,5S)-3,5-dihydroxy-2-(3-oxodecyl)cyclopentyl]hept-5-enoate, (isopropyl unoprostone);

(Z)-7-[(IR,2R,3R,5S)-3,5-dihydroxy-2-(3-oxodecyl)cyclopentyl]hept-5-enoic acid;

(−)-7-[(1R,2R)-2-(4,4-difluoro-3-oxooctyl)-5-oxocyclopentyl]heptanoic acid; and (E)-7-[(1R,2R)-2-(4,4-difluoro-3-oxooctyl)-5-oxocyclopentyl]hept-2-enoic acid.

This invention provides novel formulations of 15-keto prostaglandin drugs, 13,14-dihydro prostaglandin drugs and a 13,14-dihydro-15-keto prostaglandin drugs. A 15-keto prostaglandin drug, a 13,14-dihydro prostaglandin drug and a 13,14-dihydro-15-keto prostaglandin drug includes the drug itself, a pharmaceutically acceptable salt of the drug, or a metabolite or prodrug of the drug, as well as isomers (including tautomeric isomers) of the drug and mixtures of isomers. Preferably the drug is lubiprostone and includes its pharmaceutically acceptable salts, isomers, metabolites or prodrugs. For example, 15-hydroxy lubiprostone is a metabolite of lubiprostone, as described in U.S. Pat. No. 6,956,056. And an amide prodrug of lubiprostone is described in U.S. Pat. No. 7,064,148.

Figure 1:
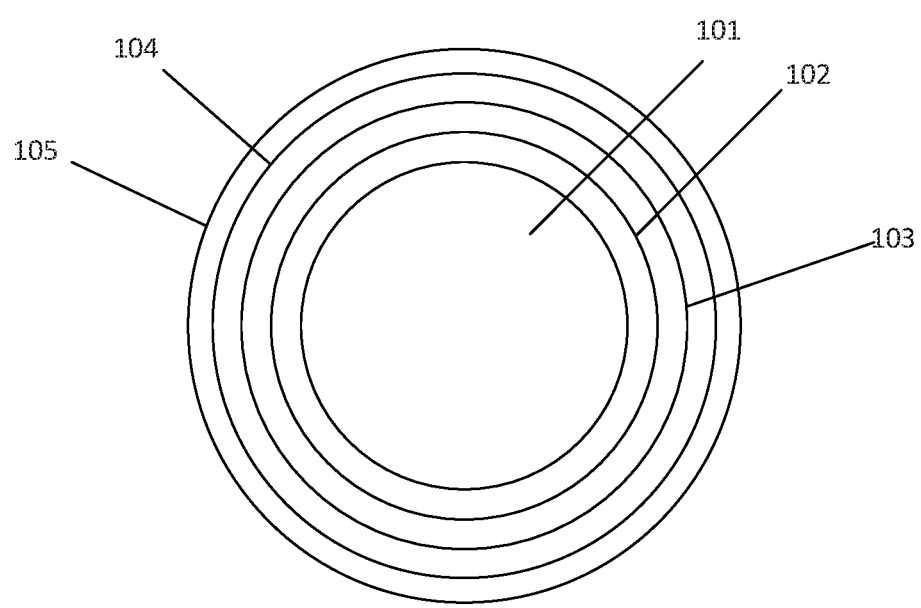
FIG. 1 depicts a multi-layer bead of the invention.

The invention relates to multilayer beads for pharmaceutical use which contain a 15-keto prostaglandin drug, a 13,14-dihydro prostaglandin drug, or a 13,14-dihydro-15-keto prostaglandin drug as the active pharmaceutical ingredient (API). FIG. 1 depicts a multi-layer bead of the invention. In a multilayer bead of the invention there is:
  (a) a core particle [101];
  (b) an optional barrier layer [102] coated on the surface of the core particle;
  (c) a drug-in-polymer layer [103] coated on the surface of the core particle or, when present, the barrier layer, wherein the drug-in-polymer layer consists essentially of:
    (i) a drug selected from the group consisting of a 15-keto prostaglandin drug, a 13,14-dihydro prostaglandin drug, and a 13,14-dihydro-15-keto prostaglandin drug; and
    (ii) a polymer selected from the group consisting of polyvinylpyrrolidone, vinylpyrrolidone-vinylacetate copolymer or a mixture thereof;
  (d) an optional sealant layer [104] coated on the surface of the drug-in-polymer layer;
and
  (e) optionally, one or more outer layers [105] external to the drug-in-polymer layer or, when present, the sealant layer.

The number and composition of such layers may be adjusted by persons skilled in the art, for example, to modify the release and stability profile of the bead and to mask its taste. However, external layers as exemplified herein are preferred.

A multilayered bead typically has a maximum size of about 2000 to about 3000 microns in diameter or along its longest axis. For example, the maximum size is about 500 to about 1000 microns or the maximum size is about 700 to about 950 microns. As with the core particle, a multilayer bead is typically spherical or spheroidal in shape but may have another shape such as, for example, an elongated shape or a lozenge shape. When used as a pediatric medicine, the diameter or longest axis of a multilayer bead of the invention should comply with the USFDA size requirements for administration to children or as a sprinkle formulation. For example, the target bead size is up to 2.5 mm with no more than a 10 percent variation over that size to a maximum size of 2.8 mm. See, USFDA Guidance for Industry, "Size of Beads in Drug Products Labeled for Sprinkle", May 2012. The amount of drug present in a multilayered bead of the invention may range from about 0.01 µg to about 0.2 µg, from about 0.02 µg to about 0.1 µg, or from about 0.04 µg to about 0.08 µg, although the amount in each bead may be adapted to the therapeutically desired dose and the number of beads present in a particular pharmaceutical composition.

The core particle [101] may be any core particle used in the pharmaceutical arts to make beaded formulations. Spherical or spheroidal particles are generally used but the core particle may be of any shape that can be coated with the other layers of the multilayer bead of the invention. The core particle may have a diameter or longest axis in the range of about 100-1,500 µm, of about 200-700 µm or of about 350-500 µm. Exemplary core particles that may be used in a multilayer bead of the invention are microcrystalline cellulose particles, silica particles and sugar particles. Microcrystalline cellulose particles having a spherical shape and a range of diameters are sold under the Cellets® tradename. Cellets® 100 are spherical microcrystalline cellulose spheres having a particle size ranging from 100-200 µm, Cellets® 350 are spherical microcrystalline cellulose spheres having a particle size ranging from 350-500 µm, Cellets® 500 are spherical microcrystalline cellulose spheres having a particle size ranging from 500-710 µm and Cellets® 1000 are spherical microcrystalline cellulose spheres having a particle size ranging from 1000-1400 µm.

In a multilayer bead of the invention an optional barrier layer [102] may be coated on the surface of the core particle. The purpose of this barrier layer is to separate the drug-in-polymer layer [103] from the core particle [101] and to minimize or prevent contact of the drug with the core. As shown below in Example 1a, contact of the drug with the core particle [101] may cause degradation of the drug and a loss of potency for the pharmaceutical formulation. The barrier layer is typically a polymeric layer. Any pharmaceutically acceptable polymer which performs the desired function of the barrier layer may be used. Preferably, the polymers are polyvinylpyrrolidone (PVP), vinylpyrrolidone-vinylacetate copolymer (PVP-VA or a mixture thereof. Various standardized PVP and PVP-VA are commercially available, for example, Kollidon® 17PF and Kollidon® VA, manufactured by BASF. Any commercially-available, pharmaceutically acceptable PVP or PVP-VA or combinations thereof may be used for the polymer matrix.

The 15-keto prostaglandin drugs, 13,14-dihydro prostaglandin drugs, or 13,14-dihydro-15-keto prostaglandin drugs which are the APIs in a multilayer bead of the invention are located in the drug-in-polymer layer [103]. A drug-in-polymer layer according to the invention consists essentially of (i) a drug selected from the group consisting of a 15-keto prostaglandin drug, a 13,14-dihydro prostaglandin drug, and a 13,14-dihydro-15-keto prostaglandin drug; and (ii) a polymer selected from the group consisting of polyvinylpyrrolidone, vinylpyrrolidone-vinylacetate copolymer or a mixture thereof. In a drug-in-polymer layer [103] the drug may exist as an amorphous solid or crystalline solid, or the drug may be molecularly dissolved in the solid excipient matrix. The drug is present in the drug-in-polymer layer in a relative amount of drug to polymer ranging from about 1 part drug per 0.2 part polymer up to about 1 part drug per 200 parts polymer, per 400 parts polymer, per 500 parts polymer per 1,000 parts polymer, and per 10,000 parts polymer.

The drug-in-polymer layer [103] may be a simple admixture of the drug and polymer or a solid dispersion of the drug in the polymer. A solid dispersion is a solid composition having at least two components where one component is dispersed in a matrix of another component. For example, the drug is dispersed as a solid in the polymeric matrix. A solid dispersion, as used herein, also includes a solid solution, wherein one component is molecularly dissolved in the solid matrix of the other component. For example, the drug is molecularly dissolved in the excipient matrix.

The drug-in-polymer layer [103] consists essentially of the drug and the polymer. The layer may, like the other layers in a multilayer bead of the invention, contain processing aids or excipients such as those discussed below. The drug-in-polymer layer [103] should not contain components which would mobilize the drug within the layer such that it might leach from into other layers of the multilayer bead or otherwise degrade. Such drug-in-polymer mixtures do not contain excipients which can affect the stability of the drug in the drug-in-polymer layer such that the drug retains therapeutic efficacy. It has been found that a drug-in-polymer layer and a multilayer bead of the invention are particularly stable even under stress stability testing conditions. After exposure to storage conditions for 10 days at 55° C., a multilayer bead of the invention retains at least 75-80% of the pharmaceutically efficacy or potency of the drug. Thus, the multilayer beads of the invention remain in a state or condition that is suitable for administration to a patient and are therapeutically efficacious without potentially interfering deterioration products.

In a multilayer bead of the invention an optional sealant layer [104] may be coated on the surface of the drug-in-polymer layer [103]. Analogous to the barrier layer [102], the purpose of this sealant layer is to separate the drug-in-polymer layer [103] from the outer layer(s) [105], when present, and to minimize or prevent the drug from leaching from the multilayer bead. As shown below in Example 1, contact of the drug with an outer layer polymer may cause degradation of the drug and a loss of potency for the pharmaceutical formulation. The sealant layer is typically a polymeric layer. Any pharmaceutically acceptable polymer which performs the desired function of the sealant layer may be used. Exemplary polymers are polyvinylpyrrolidone (PVP), vinylpyrrolidone-vinylacetate copolymer (PVP-VA) or a mixture thereof. Various standardized PVP and PVP-VA are commercially available, for example, Kollidon® 17PF and Kollidon® VA, manufactured by BASF. Any commercially-available, pharmaceutically acceptable PVP or PVP-VA or combinations thereof may be used for the polymer matrix.

In a multilayered bead of the invention, the same polymer may make up the barrier layer [103], the drug-in-polymer layer [103] and the sealant layer [104] when they are present. In such multilayer beads, the polymers in all three of these layers may be polyvinylpyrrolidone, vinylpyrrolidone-vinylacetate copolymer or a mixture thereof. In effect, the barrier layer [102] and the sealant layer [104] sandwich the drug-in-polymer layer [104] using the same polymer or mixture of polymers. If other layers are incorporated into a multilayer bead of the invention, this combination of barrier layer [103]/drug-in-polymer layer [103]/sealant layer [104] may be maintained to achieve the purposes of the layers and the stability of the multilayer bead.

A multilayer bead of the invention optionally also may contain one or more outer layers [105] to modify its release and/or taste properties, to reduce water and oxygen permeation, and/or to provide mechanical to the particle to withstand breaking or chipping. Such coatings are known in the art. For example, a coating which masks taste or prevents dissolution at neutral pH but allows rapid dissolution in acidic environment may be used to prevent dissolution or disintegration of a multilayer bead until it reaches a gastric environment after being administered as part of a pharmaceutical composition. Such polymers are, for example, insoluble at a pH ranging from 6 to 8 and soluble at pH ranging from 1 to 5 or insoluble at a pH ranging from 5 to 8 and soluble at pH ranging from 1 to 4. A wide range of copolymer systems based on methacrylic acid and methylmethacrylate systems are commercially available, such as the EUDRAGIT® polymers marketed by Evonik. In a multilayer bead of the invention, the outer layer comprises a copolymer comprising butyl methacrylate. Preferably, EUDRAGIT® E100, a copolymer of dimethylaminoethyl methacrylate, butylmethacrylate and methyl methacrylate, is used as the outer layer.

The layers of a multilayer bead, discussed above, may contain additives for coating ease as selected from pharmaceutically acceptable excipients as is known in the art. For example, one or more of the layers may contain plasticizers and lubricants such as PEGs and polyethylene glycol. Plasticizers include, for example, glycerin, acetyl tributyl citrate, polyethylene glycols, acetyl triethyl citrate, polyethylene glycol monomethyl ether, castor oil propylene glycol, diacetylated monoglycerides, sorbitol sorbitan solution, dibutyl sebacate, diethyl phthalate, triacetin, tributyl citrate and triethyl citrate. Also, each layer may be sprinkled with anti-static or static-reducers such as talc and silicon dioxide. Such materials are used in the manner and amounts known in the art, such they do not substantially interfere with the stability of the drug and multilayer bead and preferably improve the stability of the drug and prevent its migration out of the drug-in-polymer layer.

In a preferred embodiment, in a multilayer bead of the invention there is:
(a) a core particle [101];
(b) a barrier layer [102] coated on the surface of the core particle;
(c) a drug-in-polymer layer [103] coated on the surface of the core particle or, when present, the barrier layer, wherein the drug-in-polymer layer consists essentially of:
  (i) a drug selected from the group consisting of a 15-keto prostaglandin drug, a 13,14-dihydro prostaglandin drug, and a 13,14-dihydro-15-keto prostaglandin drug; and
  (ii) a polymer selected from the group consisting of polyvinylpyrrolidone, vinylpyrrolidone-vinylacetate copolymer or a mixture thereof;
(d) a sealant layer [104] coated on the surface of the drug-in-polymer layer; and
(e) one or more outer layers [105] external to the drug-in-polymer layer or, when present, the sealant layer.

This embodiment may include the various other aspects of a multilayer bead of the invention discussed above. The drug may be lubiprostone (or a pharmaceutically acceptable salt, isomer, metabolite or prodrug thereof).

A multilayer bead of the invention is prepared by sequential coating of the core particles with the indicated layers using coating techniques known in the art, such as in a fluidized bed coating apparatus. Each layer may be applied sequentially as a solution or dispersion of its components and then dried to remove the solvent prior to applying the next coating. Individual layers are spray coated using solvent. An exemplary solvent used for spray coating is acetone. The spray coating may be conducted at a temperature not exceeding 30° C. The coated layers are dried at a temperature not exceeding 45° C.

The invention also relates to pharmaceutical compositions comprising a plurality of multilayer beads according to the invention and a pharmaceutically acceptable excipient. A pharmaceutical composition of the invention may be an oral dosage form or a packaging of the multilayered beads that can be opened and the beads administered. In a pharmaceutical composition of the invention the plurality of multilayer beads may be contained in a capsule, sachet or pouch.

The invention also relates to a solid formulation of a drug in a polymer. The solid formulation of a drug in a polymer may be a simple admixture of the drug and polymer or a solid dispersion of the drug in the polymer. A solid formulation of a drug in polymer according to the invention, is a solid dispersion consisting essentially of (a) a drug selected from the group consisting of a 15-keto prostaglandin drug, a 13,14-dihydro prostaglandin drug, and a 13,14-dihydro-15-keto prostaglandin drug; and (b) a polymer selected from the group consisting of polyvinylpyrrolidone, vinylpyrrolidone-vinylacetate copolymer or a mixture thereof. Another solid formulation of a drug in a polymer according to the invention is an admixture consisting essentially of (a) a drug selected from the group consisting of a 15-keto prostaglandin drug, a 13,14-dihydro prostaglandin drug, and a 13,14-dihydro-15-keto prostaglandin drug; and (b) a polymer selected from the group consisting of polyvinylpyrrolidone, vinylpyrrolidone-vinylacetate copolymer or a mixture thereof.

A solid formulation of a drug in a polymer according to the invention may be in the form of a particle and consist essentially of (a) a drug selected from the group consisting of a 15-keto prostaglandin drug, a 13,14-dihydro prostaglandin drug, and a 13,14-dihydro-15-keto prostaglandin drug; and (b) a polymer selected from the group consisting of polyvinylpyrrolidone, vinylpyrrolidone-vinylacetate copolymer or a mixture thereof. A person skilled in the art would be able to select an appropriate particle size depending on the mode of administration, the pharmaceutical formulation containing the solid formulation, and manufacturing parameters. As an upper limit, the particle itself may be as large as approximately the size of a tablet.

The invention also relates to pharmaceutical compositions containing a solid formulation of a drug in a polymer combined with pharmaceutically acceptable excipients. In such pharmaceutical formulations, the solid formulations of a drug in a polymer may be in particle form consisting essentially of (a) a drug selected from the group consisting of a 15-keto prostaglandin drug, a 13,14-dihydro prostaglandin drug, and a 13,14-dihydro-15-keto prostaglandin drug; and (b) a polymer selected from the group consisting of polyvinylpyrrolidone, vinylpyrrolidone-vinylacetate copolymer or a mixture thereof. The solid formulation of the drug in a polymer may form the core of a multilayer bead or of a single dosage form both with one or more of the layers discussed above. The pharmaceutical composition may contain a plurality of multilayer beads.

The pharmaceutical compositions of the invention may be prepared by methods known in the pharmaceutical formulation art, for example, see Remington's Pharmaceutical Sciences, 18th Ed., (Mack Publishing Company, Easton, Pa., 1990), which is incorporated herein by reference. The layers of the bead other than the drug-in-polymer layers, and the multilayer beads themselves in a dosage form, may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, aliginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents. Acceptable excipients may also be present in between adjacent layers of the multilayer beads. For example, excipients may be present in between the outer layer and sealant layer, in between the sealant layer and drug-in-polymer layer, in between the drug-in-polymer layer and barrier layer, in between the barrier layer and the core, or combinations thereof.

Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

A pharmaceutical composition of the invention may be an oral dosage form containing a plurality of multilayered beads and other excipients to allow transport, storage and distribution. The dosage form may comprise the beads in free-flowing form or in the form of a tablet, such as a fast disintegrating tablet releasing the multilayer beads. Such a fast disintegrating tablet may for example, include a disintegrant in addition to the multilayer beads. A pharmaceutical composition of the invention may also be a solid dosage form, for example, a tablet or hard capsule, prepared, for example, as a solid solution of lubiprostone together with PVP or PVP-PA as described in the examples below. Such solid dosage forms, for example, can be made to be capable of releasing at least about 70% of the amount of drug comprised in the dosage form within 30 minutes when measured in a USP type 2 dissolution apparatus in 810 ml neutral water and 90 ml of 1N HCl at 37° C. and 200 rpm.

Solid dosage forms for oral administration such as capsules and tablets are known in the art and may be prepared by any methods well known in the art of pharmacy. See, for example, Remington's Pharmaceutical Sciences, Mack Publishing Company, Philadelphia, Pa. (18th ed. 1990). A tablet may be made by compression or molding, optimally with one or more excipient. Compressed tablets may be prepared by compressing, in a suitable machine, the active ingredient in a free-flowing form such as a powder or granules, optionally mixed with a excipient such as a binder, lubricant, inert diluent, preservative, surface-active or dispersing agent. Molded tablets may be made by molding, in a suitable machine, a mixture of the powdered compound moistened with an inert liquid diluent. The tablets may optionally be coated or scored and may be formulated so as to provide a slow or controlled release of the active ingredient therein. A capsule dosage form of the invention can be a hard capsule, and is generally made from animal-derived gelatin or plant-derived hydroxypropyl methylcellulose (HPMC). The size of a capsule for an oral dosage form of the invention can be any size that is sufficient to contain its components. For example, the capsule can be a size 5, 4, 3, 2, 1, 0, 0E, 00, 000, 13, 12, 12el, 11, 10, 7, or Su07. Capsules are filled using any suitable techniques known in the art.

The plurality of multilayer beads in combination within the pharmaceutical composition comprise a therapeutically effective amount of the drug to be administered to a patent in need thereof. The multilayer beads may be dose packed (or dosed by another appropriate dosing device, such as measuring spoon). The amount of drug present in a plurality of multilayered beads in a pharmaceutical composition of the invention may range from about 1 μg to about 75 μg, from about 4 μg to about 50 μg, or from about 8 μg to about 25 μg or in particular 8, 12, 16 or 24 μg. A unit dose of the drug is about 1 μg to about 1,500 μg, such as for example, about 1 μg to about 100 μg, such as for example, from 8 μg to about 72 μg. A pharmaceutical composition of the invention includes unit dosage forms of, for example, 8, 12, 16, 24, 48 or 72 μg, of lubiprostone (or a pharmaceutically acceptable salt, isomer, metabolite or prodrug thereof).

The invention also relates to methods of treating a gastrointestinal disorder comprising the step of orally administering to a patient in need thereof a therapeutically effective amount of the multilayer beads in a pharmaceutical composition of the invention. Accordingly, the invention relates to uses of a pharmaceutical composition of the invention to treat a gastrointestinal disorder. One such gastrointestinal disorder is constipation, and other gastrointestinal disorders include but are not limited to those associated with a dysfunctional Type 2 Chloride Channels including the disorders chronic idiopathic constipation, opioid-induced constipation, and irritable bowel syndrome with constipation. A gastrointestinal disorder treated may also be an inflammatory bowel disease, such as for example, ulcerative colitis or Crohn's disease.

It is comtemplated that formulations according to the present invention may be administered to treat gastrointestinal disorders for which the administration of lubiprostone has been approved or may be approved in the future by various national regulatory agencies. Such indications include but are not limited to: (a) the treatment of chronic idiopathic constipation (CIC) in adults; (b) the treatment of opioid-induced constipation (OIC) in adults with chronic, non-cancer pain; (c) the treatment of pediatric functional constipation (PFC) in patients aged 6 to 17 years (pending FDA approval in US at the time this application was filed); and (d) the treatment of irritable bowel syndrome with constipation (IBS-C) in women ≥18 years old. It is further contemplated that the beaded formulations according to the present invention will be helpful when administered to subjects who have dysphagia or difficulty swallowing a conventional table or capsule, particularly in children or subject. Dysphagia can occur in various disorders, for example, such as post-polio syndrome, multiple sclerosis, muscular dystrophy, Parkinson's disease, polymyositis, dermatomyositis, esophageal spasm and scleroderma.

"Treatment of" or "treating a gastrointestinal disorder" includes any means of therapeutic control such as prevention, care, relief of symptoms, attenuation of symptoms and arrest of progression. The treatment may be "long term" involving administering a pharmaceutical composition of the invention for time periods of at least two weeks, of at least three weeks, of at least one month, or at least two months or of at least six months to one year or longer. The pharmaceutical composition may be administered every day for the whole term of the treatment or with an interval of one to several days as well as once or multiple times per day.

A "therapeutically effective amount of a drug" refers to an amount of drug that elicits a therapeutically useful response in a patient in need thereof. The patient is typically a human patient but may also include other mammals such as horses, companion animals (dogs or cats), livestock and zoo animals under veterinary care. A "therapeutically effective amount" may be determined based on the age, body weight, conditions of the patient to be treated, desired therapeutic effect, administration route, treatment period and the like. Exemplary therapeutically effective amounts of lubiprostone (or a pharmaceutically acceptable salt, isomer, metabolite or prodrug thereof) may for example, be 4, 8, 12 or 24 μg once, twice or three times daily, or 48 μg once or twice daily.

A method of treatment or use of a pharmaceutical composition may include the steps of sprinkling the multilayer beads the pharmaceutical formulation into water or onto a soft food substance, and having the patient swallow the water or soft food substance with the sprinkled multilayer beads. This is particularly useful when treating gastrointestinal disorders in pediatric or geriatric patients and in the treatment of individuals aged 0-17 and/or individuals suffering from dysphagia. The multilayer beads also may be sprinkled into water (or another appropriate beverage) which may be stirred or shaken to form a suspension of the multilayer beads prior to swallowing. Soft food substances require only minimal or no chewing and include, but are not limited to, foods such as apple sauce, yogurt, ice cream, cottage cheese, baby food, baby formula, etc. Preferably a plurality of multilayer beads may be sprinkled into water and/or apple sauce. The multilayered beads of the invention can be made to be capable of resisting the release of the drug for at least about one to fifteen minutes following exposure to water or soft food substance. The multilayer particles and pharmaceutical compositions of the invention thus delay or prevent drug release into neutral suspension vehicles and in vivo prior to reaching stomach. Pharmaceutical compositions of the invention comprising the multilayer beads result in a reduction for adverse events related to nausea and vomiting when compared to prior gel capsule formulations.

EXAMPLES

Materials

The following materials were used in the examples described below:

Colloidal Silica: Aerosil® R972 Pharma, a high purity, amorphous, anhydrous, hydrophobic colloidal silica excipient available from Evonik Industries.

Microcrystalline cellulose particles (MCC spheres): Cellets® 350 spherical microcrystalline cellulose spheres having a particle size ranging from 350-500 µm, available from Glatt Pharmaceutical Services.

Dibutyl sebacate (DBS), plasticizer, which is oil (and not a solid material), available from Aldrich.

Eudragit E100, anionic copolymer based on methacrylic acid and methylmethacrylate, manufactured by Evonik Nutrition & Care GmbH.

Lubiprostone, active pharmaceutical ingredient (API).

Polyethylene glycol having a molecular weight of approximately 6000 Daltons, PEG-6000, available from TCI Chemicals.

Polyvinylpyrrolidone (PVP), also known as Povidone, Kollidon® 17PF USP, manufactured by BASF.

Polyvinylpyrrolidone-vinyl acetate copolymer (PVP-VA), also known as Copovidone, Kollidon® VA64 USP, manufactured by BASF.

Talc, lubricant, available from BRENNTAG.

Lactose, Lactose Monohydrate USP/JP, available from Maruishi Pharmaceutical.

Mannnitol: PEARLITOL® 200 SD, manufactured by Roquette.

Glucose, Dextrose USP/Glucose JP, available from Wako Pure Chemical Industries.

Hydroxy propyl cellulose (HPC), USP/JP, available from Nippon Soda.

Hydroxy propyl methyl cellulose (HPMC), also known as Hypromellose USP/JP, available from Sigma Aldrich.

Microcrystalline cellulose powder (MCC powder): CEOLUS® UF-702, manufactured by Asahi Kasei.

Corn Starch, USP/JP, available from Wako Pure Chemical Industries.

Magnesium aluminate metasillicate (MgAMS), avairable from Tomita Pharmaceutical.

Example 1A: Lubiprostone-Excipient Contact Stability Study

Test samples were prepared for the study in approximately 50:50 proportion using various excipients and lubiprostone drug. These prepared mixtures were then placed on accelerated stress stability conditions at 55° C. for 10 days. After 10 days, these samples were analyzed by a suitable HPLC method to determine assay (the amount of remaining Lubiprostone) and impurities generated due to degradation of lubiprostone. The results are shown in Table 1A.

TABLE 1A

| | Lubiprostone 55° C. 10 days | |
| --- | --- | --- |
| Excipient | Assay (% of initial) | Total Impurities |
| None (Lubiprostone Only) | 42.3% | 59.0% |
| Cellets ® 350 | 40.2% | 61.0% |
| PVP | 85.6% | 14.5% |
| PVP-VA | 83.4% | 17.7% |
| Eudragit E100 | 9.9% | 95.7% |
| PEG-6000 | 9.9% | 70.3% |
| Talc | 34.9% | 68.3% |
| DBS | 78.9% | 22.6% |
| Aerosil ® R972 Pharma | 41.5% | 61.0% |

Example 1B: Lubiprostone-Excipient Contact Stability Study (Solid Solution)

Additional test samples were prepared for the study by admixing various excipients and lubiprostone drug in ratios of about 50:50 and about 99:1. Solid solutions were prepared by mixing lubiprostone/MeCN and Excipient/MeCN, combining these mixtures and then removing the solvent by evaporation. The prepared mixtures were then placed under accelerated stress stability conditions at 55° C. for 10 days. After 10 days, these samples were analyzed by HPLC method to determine the amount of remaining lubiprostone and impurities generated as a result of the degradation of lubiprostone.

The results for the 50:50 solutions are shown in Table 1B, in which stability was relatively higher for lubiprostone in solid solution with PVP, PVP-VA and DBS. The latter (DBS) is an oil, and is a conventional plasticizer used as a film coating on granules and beads. It may be useful in some lubiprostone bead formulations as a stabilizer but is not a preferred component.

The results for the 99:1 solid solutions show relatively higher stability for lubiprostone in solid solution with PVP and PVP-VA relative to the 50:50 solid solutions. Without being held to any particular explanation, it is believed that the lubiprostone molecules are surrounded by a relatively increased number of stability-enhancing excipient molecules.

TABLE 1B

| Excipients | Solid solution 50:50 | | Solid solution 99:1 | |
|---|---|---|---|---|
| | % of the initial | 55° C. 10 d Impurities | % of the initial | 55° C. 10 d Impurities |
| Cellets | 48.4 | 31.4 | 29.3 | 51.5 |
| PVP | 86.8 | 4.7 | 100.2 | 0.0 |
| PVP-VA | 83.9 | 5.5 | 99.4 | 0.0 |
| Eudragit E | 17.6 | 73.9 | 75.5 | 11.4 |
| PEG 6000 | 14.1 | 67.8 | 24.6 | 49.2 |
| Talc | 39.3 | 40.3 | 16.3 | 70.4 |
| DBS (Liquid) | 83.5 | 7.8 | 97.6 | 1.8 |
| Aerosil | 44.9 | 34.5 | 37.4 | 42.7 |
| Lactose | 43.6 | 36.6 | 40.2 | 39.5 |
| Mannitol | 48.7 | 31.3 | 33.1 | 45.5 |
| Glucose | 46.7 | 33.6 | 33.7 | 47.5 |
| HPC | 45.0 | 34.2 | 76.8 | 12.8 |
| HPMC | 48.7 | 31.6 | 69.5 | 18.1 |
| MCC powder | 44.5 | 34.5 | 34.5 | 57.8 |
| Corn starch | 48.7 | 29.8 | 44.1 | 33.7 |
| MgAMS | 15.9 | 73.4 | — | ND |
| None Lubiprostone only | 44.4 | 33.5 | 44.4 | 35.5 |

Example 1C: Lubiprostone-Excipient Contact Stability Study (Mechanical Mixing of Powder)

Test samples were prepared by direct (mechanical) mixing of various excipients and lubiprostone drug in approximately 50:50 and 99:1 ratios. The mechanical mixing of lubiprostone and excipients was conduct by admixing them using a conventional mortar. The prepared mixtures were then placed under accelerated stress stability conditions at 55° C. for 10 days. After 10 days, these samples were analyzed by HPLC to determine the amount of remaining lubiprostone and impurities generated as a result of the degradation of lubiprostone. The results are shown in Table 1C. The observed stability increases for lubiprostone as a result of the mechanical mixing of powders was seen only with PVP and PVP-VA. The stability increase, however, was not as substantial as that observed in Example 1B for solid solutions. Without being held to any particular explanation, it is believed that this result was due to relatively less complete mixing.

TABLE 1C

| Excipients | Mechanical mixing of powder 50:50 | | Mechanical mixing of powder 99:1 | |
|---|---|---|---|---|
| | % of the initial | 55° C. 10 d Impurities | % of the initial | 55° C. 10 d Impurities |
| Cellets | 80.0 | 32.3 | Not mixable | |
| PVP | 73.5 | 9.2 | 89.5 | 7.4 |
| PVP-VA | 74.8 | 8.8 | 82.8 | 7.0 |
| Eudragit E | 23.0 | 66.1 | 43.0 | 30.4 |
| PEG 6000 | 22.6 | 56.2 | 18.5 | 57.1 |
| Talc | 47.3 | 35.6 | 18.9 | 66.5 |
| DBS (Liquid) | — | — | — | — |
| Aerosil | 48.1 | 32.6 | 79.4 | 13.0 |
| Lactose | 64.1 | 16.0 | 23.1 | 59.7 |
| Mannitol | 55.3 | 29.7 | 24.5 | 52.4 |
| Glucose | 53.1 | 20.8 | 45.3 | 29.1 |
| HPC | 58.2 | 21.9 | 73.6 | 14.4 |
| HPMC | 67.0 | 21.8 | 73.2 | 16.8 |
| MCC powder | 49.0 | 32.4 | 11.4 | 73.8 |
| Corn starch | 43.4 | 33.5 | 33.1 | 45.4 |
| MgAMS | 12.6 | 78.0 | — | |
| None Lubiprostone only | 55.6 | 24.5 | 55.6 | 24.5 |

Example 2: Lubiprostone/Polymer Layer Stability Tests

Lubiprostone/polymer solutions were prepared at 10 wt % solids in acetone (HPLC grade, EMD). About 2.5 g of each polymer solution was transferred into aluminum pans (~10 cm diameter) and dried at 40° C. for at least 4 hours, in order to form drug/polymer layers of about 100 μm thickness. The resulting films were examined visually for film integrity. All films were then placed in a forced air convection oven at 55° C. and examined for appearance changes after 10 days. The appearance of each individual drug/polymer film are summarized in Table 2.

TABLE 2

| Lubiprostone - Polymer Ratio | Polymer | t = 0 Observation | 55° C., 10 Days Observation |
|---|---|---|---|
| 1:199 | PVP | Identical to neat polymer film | No appearance change |
| 1:399 | PVP-VA | Identical to neat polymer film | No appearance change |

Example 3: Preparation of Multilayer Bead Formulations

Spherical microcrystalline cellulose particles (Cellets® 350) were sequentially covered by a polymer barrier (PVP or PVP-VA) layer, a lubiprostone (Lubi)/polymer layer, a seal coat (PVP or PVP-VA) and a water barrier outer layer (polymethacrylates Eudragit E 100), using a bottom-spray fluidized bed (VFC-LAB Micro Flo-coater) coating process at 30-60 g scale. Table 3 reports the polymers, spray solution concentrations, solvent systems, and process parameters including bed temperature ($T_{bed}$), solution feed rate (Q) and nozzle atomizing pressure (P). Coating weight was calculated by dividing the weight of polymer layer by total product weight (i.e., weight of polymer layer and substrate). A secondary tray drying step was conducted at 40° C. overnight in a forced convection oven after coating each layer to remove residual acetone.

TABLE 3

| | | Parameters | | | | |
|---|---|---|---|---|---|---|
| Polymer | Conc/ Solvent (wt %) | Air flow (LPM) | $T_{bed}$ (° C.) | Q (g/min) | P (psi) | Coating weight % |
| PVP | 6% in Acetone | 120-150 | 18-23 | 2.5-2.7 | 10.0 | 20/25* |
| PVP-VA | 6% in Acetone | 120-150 | 18-23 | 2.5-2.7 | 10.0 | 20/25* |
| Lubi: PVP = 1:199 | 6% in Acetone | 120-150 | 18-23 | 2.5-2.7 | 10.0 | 20 |
| Lubi: PVP-VA = 1:399 | | | | | | |
| Eudragit E100 | 6% in Acetone | 150-250 | 18-23 | 2.5-2.7 | 10.0 | 33 |

*Barrier coat weight = 20% and Seal coat weight = 25%

Example 4: Multi-Layer Bead Formulations and Particle Size Distribution Determination Coated beads were prepared as described in Example 3. The sequential particle size of the beads before and after coating was determined by laser diffraction using a Malvern Mastersizer 300 with an Aero S unit (Malvern Instruments). D10, D50 and D90 diameters were used to characterize the particle size distribution of powders. For instance, the D50 diameter is the diameter at which 50% of a sample's mass is comprised of smaller particles. The particle size distribution before and after each coating step was measured via laser diffraction and results are shown in Table 4 with the following abbreviations: Cellets=Cellets® 350, Lubi=Lubiprostone and E=Eudragit® E100.

TABLE 4

| Formulation | Coated Bead Description | Coating Wt % | $D_{10}$ (μm) | $D_{50}$ (μm) | $D_{90}$ (μm) |
|---|---|---|---|---|---|
| 1 | PVP Cellets | 20 | 460 | 523 | 586 |
|   | Lubi/PVP = 1/199, PVP Cellets | 20 | 476 | 561 | 657 |
|   | PVP, Lubi/PVP, PVP Cellets | 25 | 487 | 615 | 775 |
|   | E, PVP, Lubi/PVP, PVP Cellets | 33 | 540 | 709 | 935 |
| 2 | PVP-VA Cellets | 20 | 459 | 513 | 577 |
|   | Lubi/PVP-VA = 1/399, PVP-VA Cellets | 20 | 475 | 551 | 640 |
|   | PVP-VA, Lubi/PVP-VA, PVP-VA Cellets | 25 | 469 | 597 | 754 |
|   | E, PVP-VA, Lubi/PVP-VA, PVP-VA Cellets | 33 | 567 | 721 | 926 |
| 3 | PVP-VA/PEG Cellets | 20 | 460 | 509 | 573 |
|   | Lubi/PVP-VA/PEG = 1/380/20, PVP-VA/PEG Cellets | 20 | 468 | 550 | 646 |
|   | PVP-VA/PEG, Lubi/PVP-VA/PEG, PVP-VA/PEG Cellets | 25 | 494 | 605 | 738 |
|   | E, PVP-VA/PEG, Lubi/PVP-VA/PEG, PVP-VA/PEG Cellets | 33 | 568 | 713 | 903 |

As shown in Table 4, the particle size of the final products was generally smaller than 1 mm, which is a suitable size for oral suspension dosing in water or for sprinkling on soft foods.

Example 5: Dissolution Testing

A two-stage dissolution testing (i.e., neutral pH 4 gastric pH) was conducted on coated beads prepared as described in Example 3 using a Distek Model 2100C USP type 2 dissolution apparatus to simulate the dosing process and a neutral dissolution medium (HPLC grade water with 1% Kolliphor RH40, BASF) preheated to 37.0° C. All the experiments were conducted in two replicates. Analysis of samples was carried out using HPLC-MS. All three formulations show negligible drug release after being agitated in neutral dissolution medium for 1 hour and almost immediate drug release after adding 1N HCl to the medium. This indicates that multilayer beads are not only insoluble in neutral pH water but also has minimal water permeability under such conditions and then quickly dissolve once the surrounding pH decreases to gastric pH, and release drug into the medium.

Example 6—Method of Multilayer Bead Preparation

The following steps were used to prepare other batches of multilayer beads of the invention:
(a) loading a required amount of microcrystalline cellulose beads in a fluid bed coater;
(b) preparing a sub coating solution by dissolving PVP-VA in acetone and preparing a PEG 6000 aqueous solution;
(c) adding and mixing the solutions from step (b) with talc;
(d) spraying the coating solution from step (c);
(e) drying the beads after the first coating layer;
(f) further drying the beads to remove solvent;
(g) loading the beads in the fluid bed coater;
(h) charging the required amount of lubiprostone into a previously prepared solution of PVP-VA in acetone and adding PEG 6000 and talc
(i) spraying the beads with solution from step (h);
(j) drying the beads after the second coating layer;
(k) further drying the beads to remove solvent;
(l) loading the beads in the fluid bed coater;
(m) preparing a seal coating solution of PVP-VA in acetone and preparing a PEG 6000 solution and mixing with talc
(n) spraying the beads with solution from step (m);
(o) drying the beads after the second coating layer;
(p) further drying the beads to remove solvent;
(q) loading the beads in the fluid bed coater;
(r) preparing a coating solution by mixing an amino methacrylate/acetone solution with PEG 6000 and talc
(s) spraying the beads with solution from step (r);
(t) drying the beads after the second coating layer;
(u) further drying the beads to remove solvent; and
(v) sorting the beads to remove aggregates and fines.

An exemplary composition of multilayer bead of the invention is described in Table 6. Particle size testing using laser diffraction showed a D90 particle size of 0.752 mm.

TABLE 6

| Ingredient | Composition (% w/w) | Function |
|---|---|---|
| Lubiprostone | 0.024 | API |
| Microcrystalline Cellulose | 39 | Core |
| PVP-VA | 26 | API Binder & Stabilizer |
| Talc | 13 | Lubricant |
| Polyethylene Glycol | 3 | Plasticizer |
| Methacrylic acid Copolymer | 19 | Release Modifier |
| Water | * | Solvent |
| Acetone | * | Solvent |
| Total | 100 | |

*Used as solvent and removed during drying

Example 7—Method of Multilayer Bead Preparation

Another exemplary composition of multilayer bead of the invention is described in Table 7.

TABLE 7

| Ingredient | Composition (% w/w) | Function |
|---|---|---|
| Lubiprostone | 0.024 | API |
| Microcrystalline Cellulose | 26 | Core |
| Copovidone | 29 | API Binder & Stabilizer |

TABLE 7-continued

| Ingredient | Composition (% w/w) | Function |
|---|---|---|
| Talc | 15 | Lubricant |
| Polyethylene Glycol | 4 | Plasticizer |
| Methacrylic acid Copolymer | 26 | Release Modifier |
| Water | * | Solvent |
| Acetone | * | Solvent |
| Total | 100 | |

Example 8—Stability and Dissolution of Beads

Multilayer beads of the invention were tested for stability under stressed conditions. The beads were kept at 55° C. for 10 days in glass vials for stability determinations. A two-stage dissolution testing (i.e., neutral pH→gastric pH) was conducted on the beads. Dissolution testing was conducted as directed under the Paddle method (Apparatus 2), Dissolution (USP <711>) in a HCO-40: Polyoxyl 40 hydrogenated castor oil medium (known as Kolliphor RH40 (BASF)) at 37° C. Table 8 shows amount of lubiprostone remaining, appearance of related degradation substances and dissolution performance for lubiprostone beads prepared as described in Example 7. The amounts of lubiprostone and related degradation substances were assayed by HPLC. Passing criteria for the dissolution test were as follows: Stage 1 Target—Not more than 20% of the labeled amount is released in 30 mins in water with surfactant (1% HCO-40); Stage 2 Target—Not less than 60% (Q) of the labeled amount is released in 60 mins in 0.1 N HCl with surfactant (1% HCO-40).

TABLE 8

| Test item | Initial | 55° C., 10 days |
|---|---|---|
| Assay % | 105.3% | 105.5% |
| (% of the initial) | (=100%) | (100.2%) |
| Related substances | 0% | 0.2% |
| Dissolution test | Passed | passed |

Example 9—Pharmaceutical Composition: Sprinkle Beads Capsule

Multilayer beads of the invention were mixed with 0.5 wt % talc. Size 0 hypromellose blue/white sprinkle capsules are filled with the multilayer beads and talc mixture.

Example 10—Dissolution Testing: Sprinkle Beads Capsule

Figure 2:
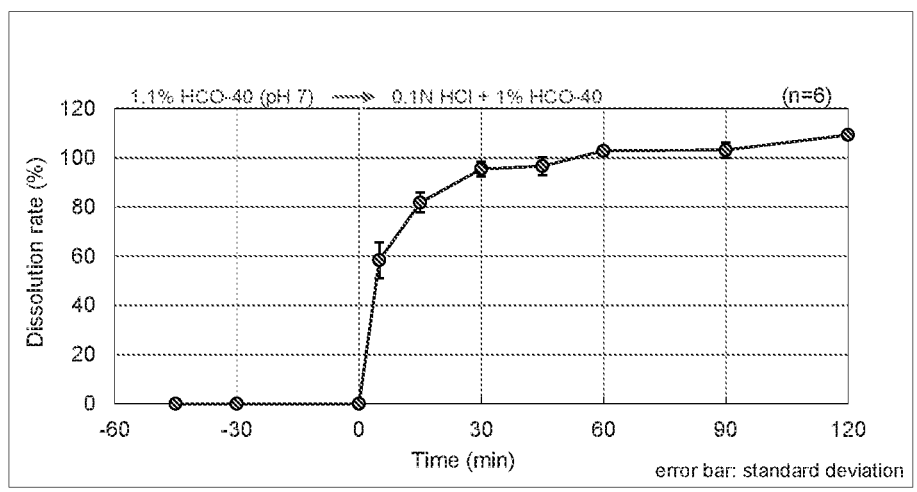
FIG. 2 depicts the dissolution profile described in Example 10.

A two-stage dissolution testing (i.e., neutral pH 4 gastric pH, described above) was conducted on a sprinkle bead capsule containing lubiprostone beads prepared as above. Multilayer beads from the capsule were sprinkled into the dissolution medium, and dissolution testing was conducted as described in Example 8. FIG. 2 shows the dissolution profile with minimal to no drug release in the neutral aqueous environment and that the entire remaining drug is released in an acidic environment (like the stomach).

Example 11—Stability and Dissolution of Sprinkle Beads Capsule

Sprinkle beads in hypromellose capsules, with 24 μg lubiprostone with multilayer beads, prepared as described above, was tested for stability and dissolution. The stability study was conducted using HDPE screw top bottles with desiccant. Stability data for up to 3 months at 25° C./60% RH and at 40° C./75% RH is shown in Tables 9 and 10. As shown below, the batch shows good stability.

TABLE 9

Stability Testing at 25° C./60% RH

| Test item | | | Initial | 1 month | 3 months |
|---|---|---|---|---|---|
| Description | | | White (body) and blue (cap) hard HPMC capsules filled with white beads | Not changed | Not changed |
| Identification (HPLC) | | | Conforms | — | — |
| Assay | | | 94.2% | 93.7% | 92.3% |
| (% of the initial) | | | (=100%) | (99.5%) | (98.0%) |
| Related substances | | | 0% | 0% | 0% |
| Dissolution test | Stage 1 | 15 min | 2.6% | 1.5% | 0.0% |
| | | 30 min | 2.7% | 2.4% | 0.0% |
| | | 60 min | 3.6% | 3.4% | 0.0% |
| | Stage 2 | 5 min | 49.4% | 61.9% | 56.9% |
| | | 15 min | 70.5% | 78.2% | 69.7% |
| | | 30 min | 83.4% | 89.2% | 82.9% |
| | | 45 min | 84.8% | 91.1% | 92.1% |
| | | 60 min | 89.9% | 92.8% | 94.2% |
| | | 90 min | 99.4% | 96.4% | 89.4% |
| | | 120 min | 105.8% | 103.1% | 96.4% |

TABLE 10

Stability Testing at 40° C./75% RH

| Test item | | | Testing point | | | |
|---|---|---|---|---|---|---|
| | | | Initial | 1 month | 2 months | 3 months |
| Description | | | White (body) and blue (cap) hard HPMC capsules filled with white beads | Not changed | Not changed | Not changed |
| Identification (HPLC) | | | Conforms | — | — | — |
| Assay (% of the initial) | | | 94.2% (=100%) | 91.7% (97.4%) | 92.9% (98.6%) | 91.6% (97.2%) |
| Related substances | | | 0% | 0% | 0.2% | 0.2% |
| Dissolution test | Stage 1 | 15 min | 2.6% | 0.0% | 0.0% | 0.0% |
| | | 30 min | 2.7% | 0.0% | 0.0% | 0.0% |
| | | 60 min | 3.6% | 0.0% | 1.1% | 0.9% |
| | Stage 2 | 5 min | 49.4% | 59.9% | 78.4% | 47.6% |
| | | 15 min | 70.5% | 76.9% | 91.1% | 69.3% |
| | | 30 min | 83.4% | 83.3% | 92.8% | 77.2% |
| | | 45 min | 84.8% | 92.3% | 93.9% | 79.3% |
| | | 60 min | 89.9% | 91.3% | 94.7% | 81.7% |
| | | 90 min | 99.4% | 97.4% | 95.0% | 95.9% |
| | | 120 min | 105.8% | 99.7% | 97.9% | 98.9% |

Example 12—Stability of Sprinkle Beads in Capsule with Apple Sauce

An in-vitro test was conducted to establish the chemical compatibility of the drug lubiprostone in an intended dosing vehicle (apple sauce). Sprinkle beads from one capsule (beads containing 24 μg of lubiprostone) were combined with Apple sauce, TREE TOP Apple Sauce (no sugar added), 5 g (on a teaspoon). The beads were kept at room temperature and sampled at 0, 5, 10, 20 min.

After sprinkling the contents of a capsule onto apple sauce, the beads were recovered by decantation and rinsing (with water), and then the API content of the beads (assay) was determined. The results are shown below in Table 11 and these indicate good chemical compatibility of the beads when mixed with apple sauce for up to 20 mins (although it is expected to be consumed by patients in the first 5 minutes). The results also confirm that functional coating (acid-dissolving layer) prevents the API from leaking from the bead formulation when sprinkled on apple sauce.

TABLE 11

| Assay results | 0 min | 5 min | 10 min | 20 min |
|---|---|---|---|---|
| Beads on Apple sauce (Remaining API %) | 97.7% | 97.2% | 97.1% | 93.2% |

The invention includes all embodiments and variations substantially as hereinbefore described and with reference to the examples and figures. Although various embodiments of the invention are disclosed herein, adaptations and modifications may be made within the scope of the invention in accordance with the common general knowledge of those skilled in this art.

The claimed invention is:

1. A multilayer bead comprising:
   (a) a core particle, wherein the core particle is drug-free;
   (b) an optional barrier layer coated on the surface of the core particle;
   (c) a drug-in-polymer layer coated on the surface of the core particle or, when present, the barrier layer, wherein the drug-in-polymer layer comprises:
      (i) a drug selected from the group consisting of a 15-keto prostaglandin drug, a 13,14-dihydro prostaglandin drug, and a 13,14-dihydro-15-keto prostaglandin drug; and
      (ii) a polymer selected from the group consisting of polyvinylpyrrolidone, vinylpyrrolidone-vinylacetate copolymer, and a mixture thereof;
   (d) an optional sealant layer coated on the surface of the drug-in-polymer layer; and
   (e) optionally one or more outer layers external to the drug-in-polymer layer or, when present, the sealant layer.

2. The multilayer bead of claim 1, wherein the core particle is selected from the group consisting of microcrystalline cellulose particles, silica particles, and sugar particles.

3. The multilayer bead of claim 1, wherein the drug is selected from the group consisting of:
   (−)-7-[(2R,4aR,5R,7aR)-2-(1,1-difluoropentyl)-2-hydroxy-6-oxooctahydrocyclopenta[b]pyran-5-yl]heptanoic acid, (lubiprostone);
   (−)-7-{(2R,4aR,5R,7aR)-2-[(3S)-1,1-difluoro-3-methylpentyl]-2-hydroxy-6-oxooctahydrocyclopenta[b]pyran-5-yl}heptanoic acid, (cobiprostone);
   (+)-isopropyl (Z)-7-[(1R,2R,3R,5S)-3,5-dihydroxy-2-(3-oxodecyl)cyclopentyl]hept-5-enoate, (isopropyl unoprostone);
   (Z)-7-[(1R,2R,3R,5S)-3,5-dihydroxy-2-(3-oxodecyl)cyclopentyl]hept-5-enoic acid;
   (−)-7-[(1R,2R)-2-(4,4-difluoro-3-oxooctyl)-5-oxocyclopentyl]heptanoic acid; and
   (E)-7-[(1R,2R)-2-(4,4-difluoro-3-oxooctyl)-5-oxocyclopentyl]hept-2-enoic acid.

4. The multilayer bead of claim 1, wherein the drug is present in an amount from about 0.01 μg to about 0.2 μg.

5. The multilayer bead of claim 1, wherein the drug and the polymer are present in a relative amount from about 1 part drug per about 0.2 part polymer to about 1 part drug per about 10,000 parts polymer.

6. The multilayer bead of claim 1, wherein the barrier layer is present and comprises a polymer selected from the group consisting of polyvinylpyrrolidone, vinylpyrrolidone-vinylacetate copolymer, and a mixture thereof.

7. The multilayer bead of claim 1, wherein the sealant layer is present and comprises a polymer selected from the group consisting of polyvinylpyrrolidone, vinylpyrrolidone-vinylacetate copolymer, and a mixture thereof.

8. The multilayer bead of claim 1, wherein at least one outer layer is present and comprises a polymer that insoluble at a pH ranging from 5 to 8 and is soluble at pH ranging from 1 to 4, or a polymer that is insoluble at a pH ranging from 6 to 8 and is soluble at pH ranging from 1 to 5.

9. The multilayer bead of claim 1, wherein at least one outer layer is present and comprises a methacrylate-based polymer.

10. The multilayer bead of claim 1, wherein the barrier layer is present and comprises a polymer selected from the group consisting of polyvinylpyrrolidone, vinylpyrrolidone-vinylacetate copolymer, and a mixture thereof, and the sealant layer is present and comprises a polymer selected from the group consisting of polyvinylpyrrolidone, vinylpyrrolidone-vinylacetate copolymer, and a mixture thereof.

11. The multilayer bead of claim 10, wherein:
   (a) the core particle comprises microcrystalline cellulose;
   (b) the barrier layer comprises a vinylpyrrolidone-vinyl acetate copolymer;
   (c) the drug-in-polymer layer comprises a therapeutically effective amount of lubiprostone or a pharmaceutically acceptable salt or isomer thereof and a vinylpyrrolidone-vinyl acetate copolymer; and
   (d) the sealant layer comprises a vinylpyrrolidone-vinyl acetate copolymer.

12. The multilayer bead of claim 1, wherein:
   (a) the core particle comprises microcrystalline cellulose;
   (b) the barrier layer is present and comprises a vinylpyrrolidone-vinyl acetate copolymer;
   (c) the drug-in-polymer layer comprises a therapeutically effective amount of lubiprostone or a pharmaceutically acceptable salt or isomer thereof and a vinylpyrrolidone-vinyl acetate copolymer;
   (d) the sealant layer is present and comprises a vinylpyrrolidone-vinyl acetate copolymer; and
   (e) one outer layer is present and comprises a copolymer comprising butyl methacrylate.

13. The multilayer bead of claim 12, wherein the barrier layer, drug-in-polymer layer, sealant layer, outer layer, or any combination thereof comprises one or more pharmaceutically acceptable excipients.

14. The multilayer bead of claim 13, wherein the one or more pharmaceutically acceptable excipients is talc, polyethylene glycol, or a combination thereof.

15. The multilayer bead of claim 12, wherein lubiprostone is present in an amount from about 0.01 µg to about 0.2 µg.

16. The multilayer bead of claim 15, wherein the amount of lubiprostone is from about 0.04 µg to about 0.08 µg.

17. The multilayer bead of claim 12, wherein lubiprostone and the vinylpyrrolidone-vinyl acetate copolymer are present in a relative amount from about 1 part lubiprostone per about 0.2 part vinylpyrrolidone-vinyl acetate copolymer to about 1 part lubiprostone per about 10,000 parts vinylpyrrolidone-vinyl acetate copolymer.

18. The multilayer bead of claim 17, wherein the relative amount of lubiprostone and the vinylpyrrolidone-vinyl acetate copolymer is from about 1 part lubiprostone per about 200 parts vinylpyrrolidone-vinyl acetate copolymer to about 1 part lubiprostone per about 1,000 parts vinylpyrrolidone-vinyl acetate copolymer.

19. A pharmaceutical composition comprising a plurality of multilayer beads according to claim 1 and at least one pharmaceutically acceptable excipient.

20. The pharmaceutical composition of claim 19, wherein the plurality of multilayer beads is contained in a capsule, a sachet, or a pouch.

21. The pharmaceutical composition of claim 20, wherein the capsule is a sprinkle capsule.

22. The pharmaceutical composition of claim 19, wherein the plurality of multilayer beads provides from about 1 pg to about 75 pg of the drug.

23. The pharmaceutical composition of claim 22, wherein the drug is lubiprostone.

24. A method for treating a gastrointestinal disorder, the method comprising orally administering to a patient in need thereof a therapeutically effective amount of the multilayer beads in the pharmaceutical composition of claim 19.

25. The method of claim 24, further comprising sprinkling the multilayer beads in pharmaceutical composition into water or onto a soft food substance prior to orally administering to the patient.

26. The method of claim 24, wherein the gastrointestinal disorder is selected from the group consisting of chronic idiopathic constipation, opioid-induced constipation, and irritable bowel syndrome with constipation.

27. The method of claim 24, wherein the patient is a pediatric patient or a geriatric patient.

* * * * *